United States Patent
Hausman (10) Patent No.: US 10,342,666 B2
(45) Date of Patent: Jul. 9, 2019

(54) METHOD OF STABILIZING A PATIENTS ULNOHUMERAL JOINT

(71) Applicant: TriMed, Incorporated, Santa Clarita, CA (US)

(72) Inventor: Michael Hausman, New York, NY (US)

(73) Assignee: Trimed, Incorporated, Santa Clarita, CA (US)

( * ) Notice: Subject to any disclaimer, the term of this patent is extended or adjusted under 35 U.S.C. 154(b) by 114 days.

(21) Appl. No.: 15/381,961

(22) Filed: Dec. 16, 2016

(65) Prior Publication Data
US 2018/0021142 A1 Jan. 25, 2018

Related U.S. Application Data

(60) Provisional application No. 62/365,462, filed on Jul. 22, 2016.

(51) Int. Cl.
*A61F 2/38* (2006.01)
*A61F 2/46* (2006.01)
*A61F 2/30* (2006.01)

(52) U.S. Cl.
CPC .......... *A61F 2/3804* (2013.01); *A61F 2/4605* (2013.01); *A61F 2002/3085* (2013.01); *A61F 2002/30224* (2013.01); *A61F 2002/3813* (2013.01); *A61F 2002/3831* (2013.01)

(58) Field of Classification Search
CPC ............ A61F 2/3804; A61F 2002/3813; A61F 2/4605
See application file for complete search history.

(56) References Cited

U.S. PATENT DOCUMENTS

| | | | | |
|---|---|---|---|---|
| 7,297,165 B1* | 11/2007 | Kriek | ..................... | A61F 2/3804 623/18.11 |
| 8,025,667 B2* | 9/2011 | Grant | ................. | A61B 17/1728 606/102 |
| 8,668,693 B2* | 3/2014 | Bernstein | ............ | A61B 17/1725 606/64 |
| 2004/0116930 A1* | 6/2004 | O'Driscoll | ......... | A61B 17/8061 606/281 |
| 2005/0049710 A1* | 3/2005 | O'Driscoll | ............ | A61F 2/3804 623/20.11 |
| 2009/0105819 A1* | 4/2009 | Barry | ................. | A61B 17/1615 623/17.11 |
| 2010/0063549 A1* | 3/2010 | Orbay | ................... | A61F 2/3804 606/281 |
| 2010/0137866 A1* | 6/2010 | Gelfand | ............. | A61B 17/8061 606/70 |

(Continued)

*Primary Examiner* — David H Willse
*Assistant Examiner* — Javier Blanco
(74) *Attorney, Agent, or Firm* — Wood, Phillips, Katz, Clark & Mortimer (57) ABSTRACT

A method of stabilizing a patient's ulnohumeral joint including the steps of: obtaining a stabilizing assembly having a mounting portion and a buttressing portion; and implanting the stabilizing assembly into an operative position wherein the mounting portion of the stabilizing assembly is anchored at a proximal region of the patient's ulna and the buttressing portion is situated to abut the patient's humerus so as to limit subluxation at the ulnohumeral joint while allowing movement between the patient's ulna and humerus at the patient's ulnohumeral joint.

15 Claims, 6 Drawing Sheets (56) References Cited

U.S. PATENT DOCUMENTS

| | | | | |
|---|---|---|---|---|
| 2011/0125265 A1* | 5/2011 | Bagga | ................ | A61B 17/68 623/16.11 |
| 2011/0172781 A1* | 7/2011 | Katrana | ............... | A61F 2/3804 623/20.11 |
| 2011/0218532 A1* | 9/2011 | Eglseder | ............... | A61B 17/56 606/64 |

* cited by examiner

METHOD OF STABILIZING A PATIENTS ULNOHUMERAL JOINT

BACKGROUND OF THE INVENTION

Field of the Invention

This invention relates to human elbows and, more particularly, to a method of stabilizing the ulnohumeral joint against subluxation and dislocation.

Background Art

The bones that make up the human elbow are the humerus, the ulna, and the radius. The ulna and the humerus cooperate at one joint location. Ligaments maintain the humerus connected to the ulna and provide stability at this joint.

Traumatic dislocations of the elbow generally occur in conjunction with fractures around the elbow joint and injury to the ligaments of the elbow. This combination of a fracture and a ligament injury may render the elbow unstable and prone to subluxation and dislocation.

Fractures of the radial head are usually treatable by fixation of the fracture or replacement of the radius that, combined with ligament repair, restore stability to the elbow.

Fracture of the coronoid process of the proximal ulna may not be repairable and there is no coronoid replacement. In such cases, it may not be possible to stabilize the elbow joint in a concentric position without coronoid support, that is essential for elbow stability.

Current treatment of such instability involves radical, non-physiologic treatment such as external fixation, placement of a temporary fracture fixation plate across the elbow, or pin or screw fixation. Oftentimes even these measures cannot adequately stabilize the elbow joint.

Generally, existing treatments for coronoid deficient elbows involve immobilization of the patient's upper arm and forearm for periods adequate to allow ligament healing and/or healing of a reconstructed coronoid. This immobilization is inconvenient and often involves use of invasive and intrusive internal and external components. Further, the surgeries performed to make the repairs may be quite complicated.

At the same time, the conventional procedures often do not reliably maintain the integrity and stability of the elbow adequate to promote its healing. Re-dislocation is known to commonly occur.

In spite of the above problems, the above type of procedures have been consistently practiced since no alternative procedures are known that effectively stabilize primarily the ulnohumeral joint without complicated procedures and structures and inconvenient immobilization.

SUMMARY OF THE INVENTION

In one form, the invention is directed to a method of stabilizing a patient's ulnohumeral joint including the steps of: obtaining a stabilizing assembly having a mounting portion and a buttressing portion; and implanting the stabilizing assembly into an operative position wherein the mounting portion of the stabilizing assembly is anchored at a proximal region of the patient's ulna and the buttressing portion is situated to abut the patient's humerus so as to limit subluxation at the ulnohumeral joint while allowing movement between the patient's ulna and humerus at the patient's ulnohumeral joint.

In one form, the step of implanting the stabilizing assembly involves directing the stabilizing assembly from a starting position, externally of the patient's elbow, through the patient's ulna and into the operative position.

In one form, the step of obtaining a stabilizing assembly involves obtaining a stabilizing assembly in the form of an elongate peg.

In one form, the elongate peg has mounting threads at the mounting portion. A tapered portion facilitates guided movement of the peg through the patient's ulna as the stabilizing assembly is changed from the starting position into the operative position.

In one form, the peg has an elongate body with a length and leading and trailing ends spaced in a lengthwise direction. The mounting portion is at the trailing end and the tapered portion is at the leading end.

In one form, the body has a lengthwise passage extending fully through the body between the leading and trailing ends.

In one form, the step of implanting the stabilizing assembly includes the step of directing a guide wire through the patient's ulna in a predetermined path and into an operative position.

In one form, the step of implanting the stabilizing assembly includes the step of creating a pilot hole through the patient's ulna by directing a cannulated drill through the patient's ulna guidingly against the operatively positioned guide wire.

In one form, the step of implanting the stabilizing assembly includes the step of directing the peg, leading end first, through the pilot hole.

In one form, the step of directing the peg through the pilot hole involves the step of using the operatively positioned guide wire to guide the peg leading end through the pilot hole.

In one form, the body has a lengthwise passage extending fully through the body between the leading and trailing ends. The step of using the operatively positioned guide wire to guide the peg leading end involves sliding the body along the guide wire with the guide wire extending through the lengthwise passage.

In one form, the step of implanting the stabilizing assembly further involves the step of engaging the mounting threads with the patient's ulna.

In one form, the tapered portion of the stabilizing assembly bears against the humerus with the stabilizing assembly in the operative position.

In one form, the elongate body has a single piece that defines the mounting and tapered portions.

In one form, the stabilizing assembly is implanted to stabilize the patient's ulnohumeral joint that is damaged and destabilized by reason of being damaged. The method further includes the step of removing the stabilizing assembly after the stabilizing assembly is implanted for a selected healing period.

In one form, the stabilizing assembly extends through the patient's ulna at the patient's coronoid.

In one form, the elongate body has a cylindrical cross-sectional configuration.

In one form, the patient's ulna has a length along a first line. The length of the elongate body extends along a second line. The first and second lines make an angle of 35°-65° with respect to each other.

In one form, the first and second lines make an angle with each other that is on the order of 50°.

In one form, the invention is directed to a stabilizing assembly as described above.

DETAILED DESCRIPTION OF THE PREFERRED EMBODIMENT

Figure 1:
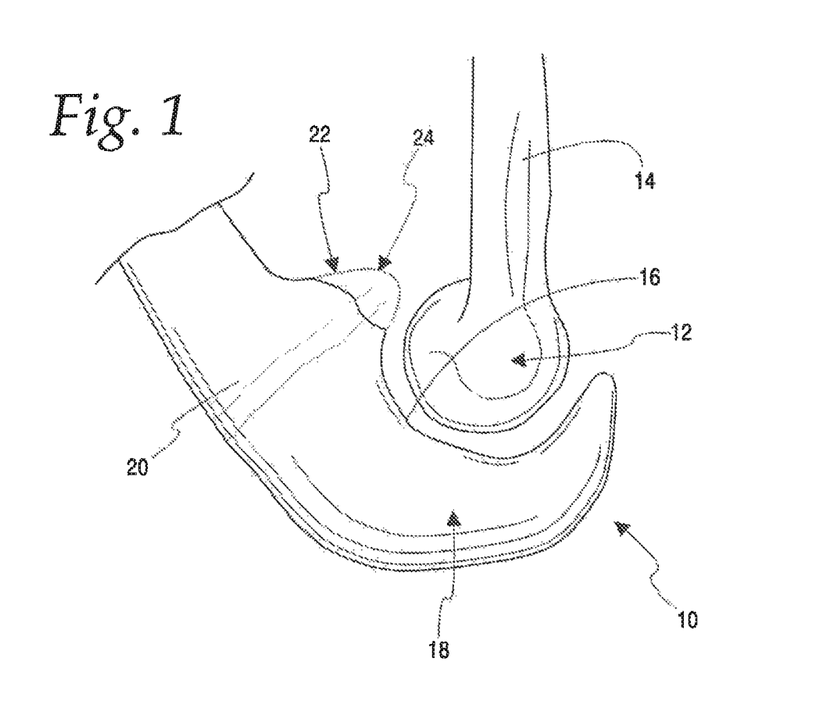
FIG. 1 is a fragmentary, partially schematic representation of a patient's ulnohumeral joint with a deficiency in the coronoid region.
Figure 2:
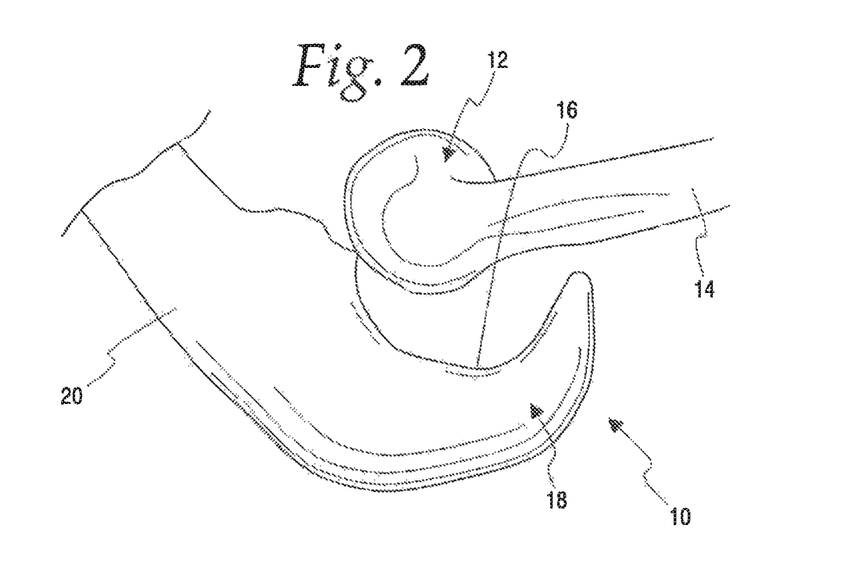
FIG. 2 is a view as in FIG. 1 showing subluxation of the ulnohumeral joint in FIG. 1.

At the ulnohumeral joint 10 on the human elbow, as shown in FIGS. 1, 2, and 7-10, the lower head region 12 of the humerus 14 is allowed to hinge within a socket 16 at a proximal region 18 of the ulna 20. As depicted in FIG. 1, the coronoid region at 22 interacts with the humeral head 12 to prevent subluxation of the ulnohumeral joint 10 and incongruency, as shown in FIG. 2. The coronoid process at 24, in a healthy joint, has generally the configuration shown in dotted lines in FIG. 1. In FIG. 1, the coronoid region 22 is shown in solid lines with a deficiency that may result from a fracture, a deformation, or another cause. With this coronoid deficiency, the ulnohumeral joint 10 is unstable, which condition is prevented primarily by ligaments and muscles that may become extended due to injury.

Figure 3:
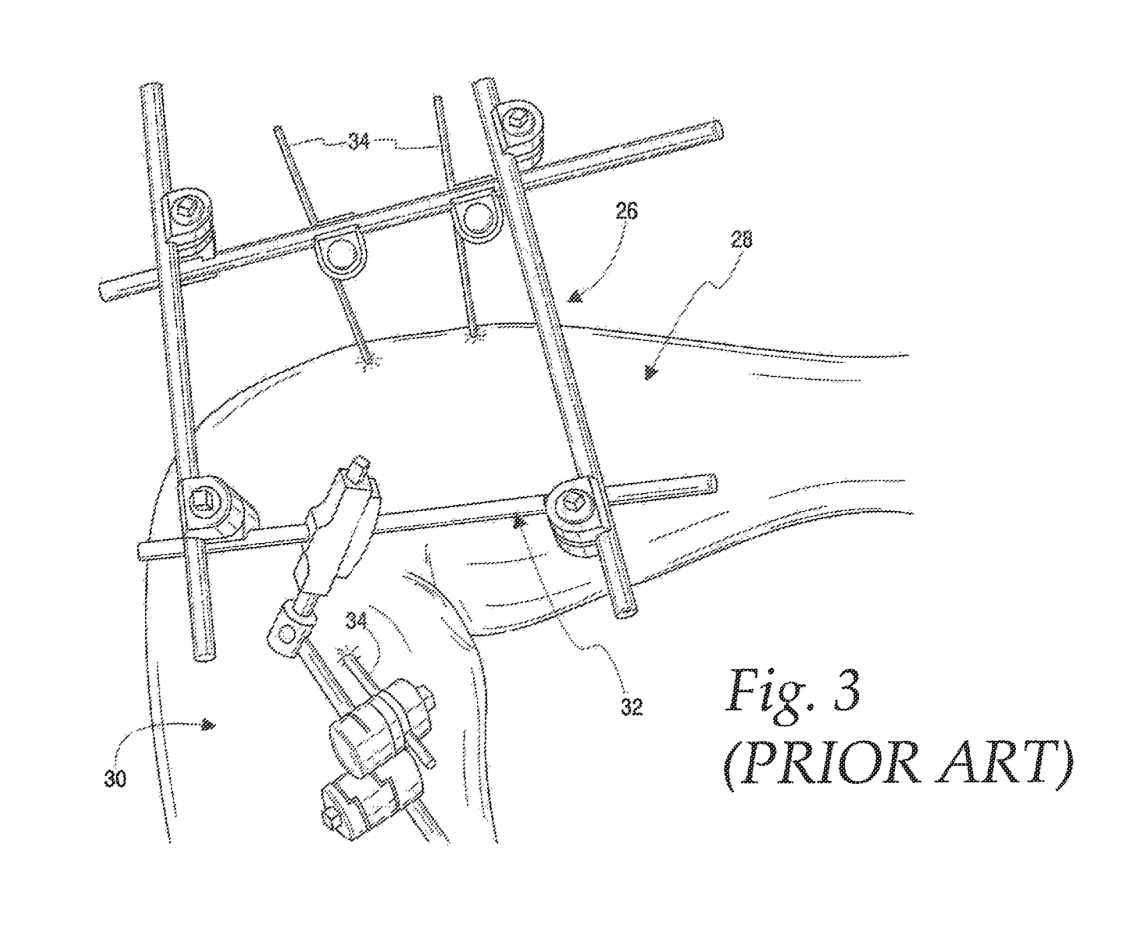
FIG. 3 is a fragmentary elevation view of a patient's forearm and upper arm immobilized using a conventional external fixation device.

As noted above, external fixation is commonly utilized to immobilize the arm to allow healing of the muscles and ligaments and potentially a rebuilding of the coronoid process 24. As shown in FIG. 3, an external fixation device 26, of conventional construction, attaches to both the patient's forearm 28 and upper arm 30 and has an associated frame at 32 that can be adjusted to control a relationship between the forearm and upper arm that is to be maintained. Adjustable rods 34 extend from the frame 32 to the internal arm bones—the humerus, ulna, and radius.

Figure 4:
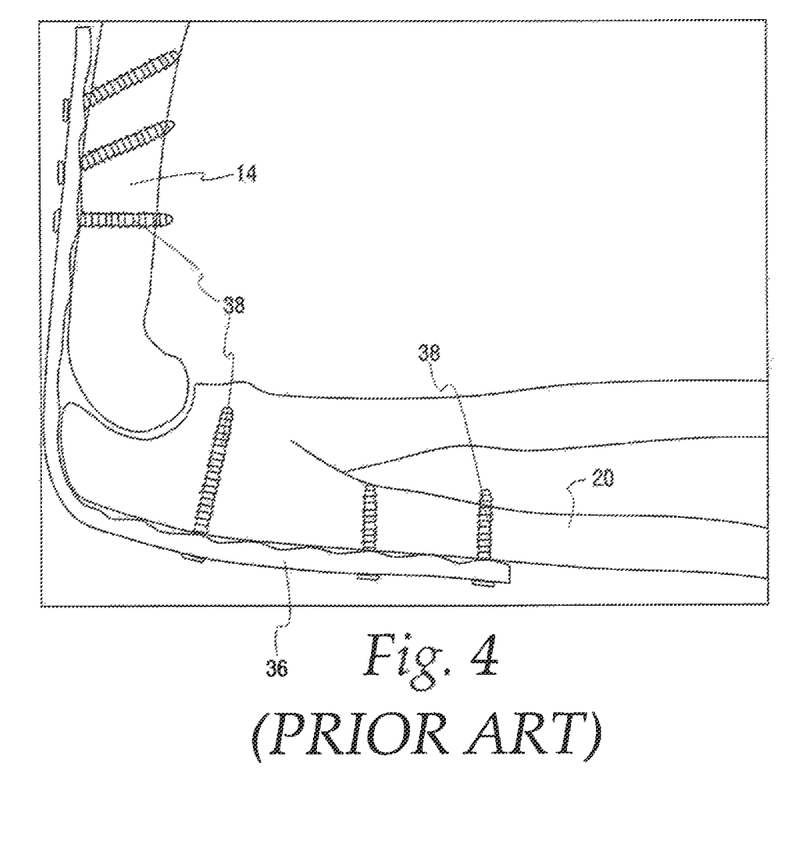
FIG. 4 is a fragmentary, elevation view of a conventional plate used to immobilize a patient's humerus and ulna.

An alternative prior art immobilization system is shown in FIG. 4. A generally L-shaped fixation plate 36 is conformed to the patient's ulna 20 and humerus 14 and secured through a series of fasteners 38. The angle produced by the "L" is selected to maintain the ulna 20 and humerus 14 at a corresponding immobilization angle to optimally promote healing.

Figure 5:
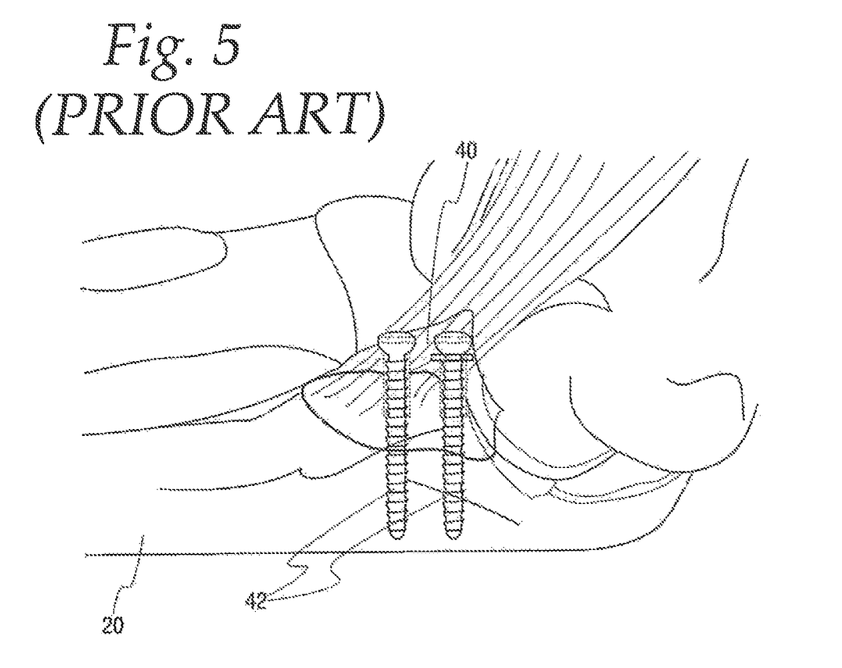
FIG. 5 is a fragmentary, elevation view of an ulnohumeral joint with a coronoid fragment repaired using one conventional method.

In FIG. 5, a fractured fragment 40 of the coronoid process is conventionally secured through fasteners 42 to the ulna 20.

Figure 6:
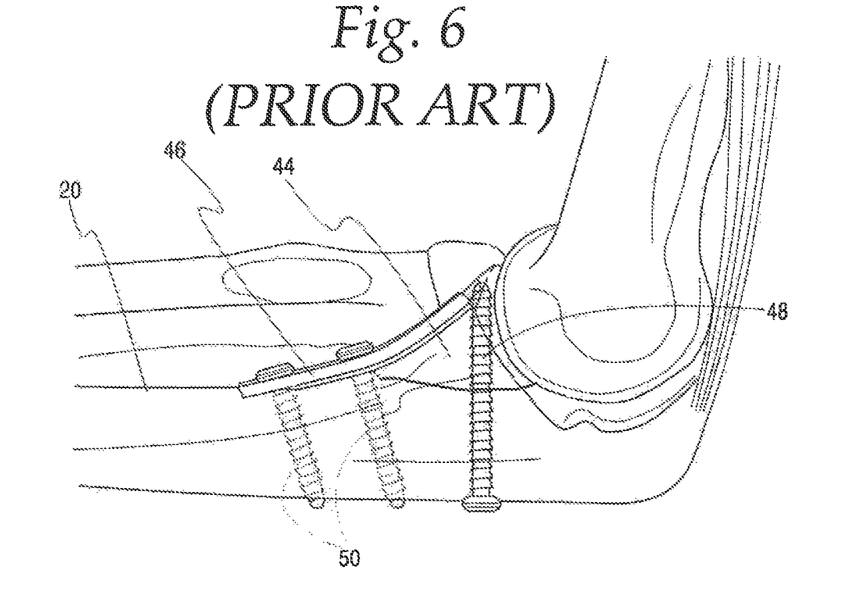
FIG. 6 is a view as in FIG. 5 wherein a larger fragment of the coronoid region is conventionally repaired.

With a larger fragment 44, as shown in FIG. 6, a conventional plate 46 is used in conjunction with fasteners to fix the fragment 44. One fastener 48 is shown directed through the ulna 20 into the fragment 44. The plate 46 is secured to a stable portion of the ulna 20 using additional fasteners 50.

A method of stabilizing a patient's ulnohumeral joint 10, according to the invention, is shown in FIGS. 7-10. The coronoid deficiency, as described with respect to FIGS. 1 and 2, is present.

Figure 9:
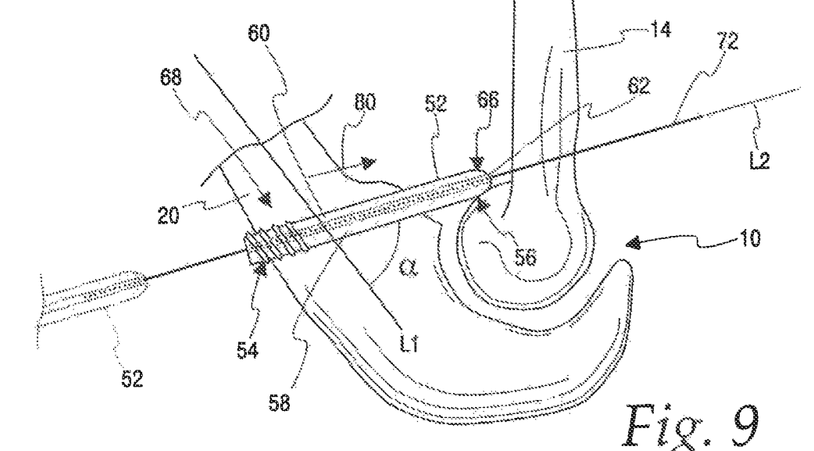
Figure 10:
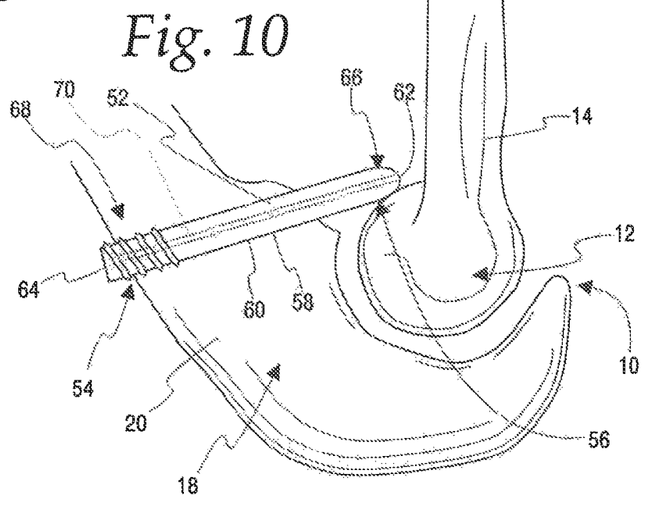

A stabilizing assembly 52 is obtained and has a mounting portion at 54 and a buttressing portion at 56. The stabilizing assembly 52 is implanted into an operative position, as shown in FIGS. 9 and 10, wherein the mounting portion 54 of the stabilizing assembly 52 is anchored in the proximal ulnar region at 18 and the buttressing portion 56 is situated to abut the head region 12 of the humerus 14. This effectively restores the function of the deteriorated coronoid process so as to limit subluxation at the ulnohumeral joint 10. Because the stabilizing assembly 52 does not penetrate the humerus 14 in a manner to inhibit hinging movement of the humerus 14 and ulna 20, normal movement between the ulna 20 and humerus 14 is permitted without concern about subluxation or re-dislocation.

Figure 11:
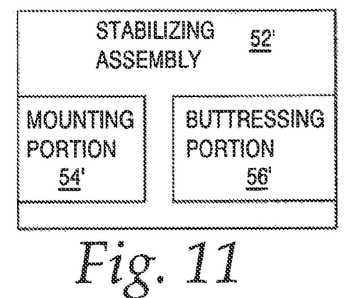
FIG. 11 is a schematic representation of the inventive stabilizing assembly.

In FIG. 11, a generic form of the inventive stabilizing assembly is shown at 52' in schematic form. The schematic showing of the stabilizing assembly 52' is intended to encompass the specific form described herein and virtually an unlimited number of variations thereof. Essentially, the stabilizing assembly 52' requires only a mounting portion 54' that can be anchored to the ulna 20 in any manner that a stabilized buttressing portion 56' will be situated to interact with the humeral head 12 to avoid subluxation or re-dislocation in the same general manner as described for the stabilizing assembly 52. One specific form of stabilizing assembly is shown in FIGS. 9 and 10. However, this form is exemplary in nature only, as the invention contemplates any structure that stabilizes a buttressing portion to interact with the humerus 14 as depicted to confine movement of the head region of the humerus 14 within the socket 16 on the ulna 20.

The exemplary stabilizing assembly 52 is in the form of an elongate peg 58 with an elongate body 60 with a length between leading and trailing ends 62, 64, spaced from each other in a lengthwise direction. The mounting portion 54 is at the trailing end 64. A tapered portion 66, at the leading end 62, facilitates guided movement of the body 60 through bone, muscle, and ligaments, as hereinafter described. The mounting portion 54 includes threads 68.

In a preferred form, the elongate body 60 has a cylindrical cross-sectional configuration along its length. While not required, the body 60 has a single piece that defines the mounting and tapered portions 54, 66.

The body 60 has a lengthwise passage 70 extending fully through the body 60 between the leading and trailing ends 62, 64.

In the depicted form, the implantation of the stabilizing assembly 52 involves directing the stabilizing assembly 52 from a starting position, externally of the patient's elbow, through the patient's ulna 20 and into the operative position in FIGS. 9 and 10. In FIG. 9, the starting position for the stabilizing assembly 52 is shown in dotted lines, with the operative position shown in solid lines in that same figure.

Figure 7:
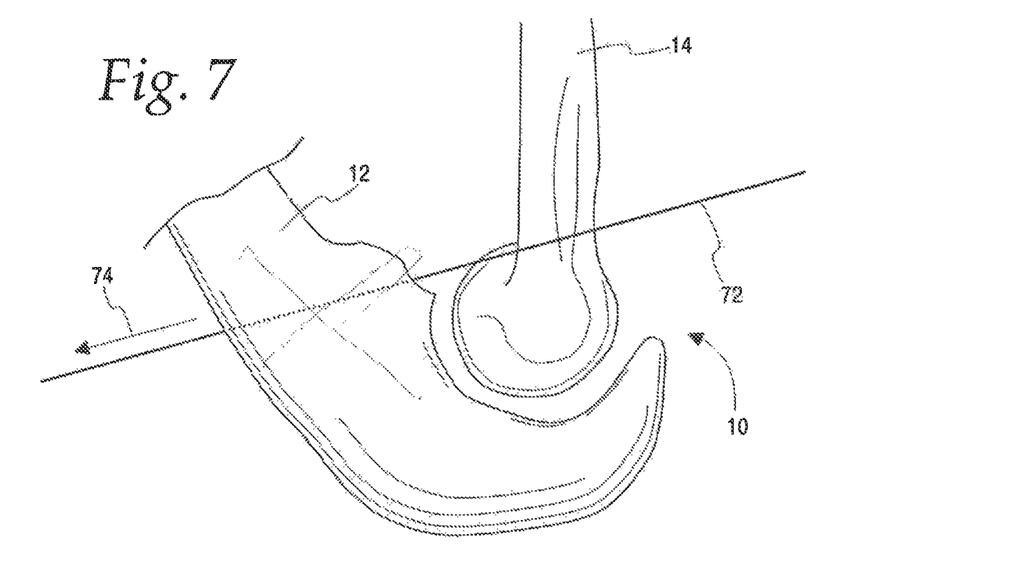
FIGS. 7-10 show steps performed sequentially in implanting a stabilizing assembly, according to the invention, into an operative position.

In a preferred form, the first step of implanting the stabilizing assembly 52 involves directing a guide wire 72 in the direction of the arrow 74 past the humerus 14 and through the ulna 20 in a predetermined path into the operative position shown in FIG. 7. The guide wire 72 may have a diameter on the order of 0.045".

Figure 8:
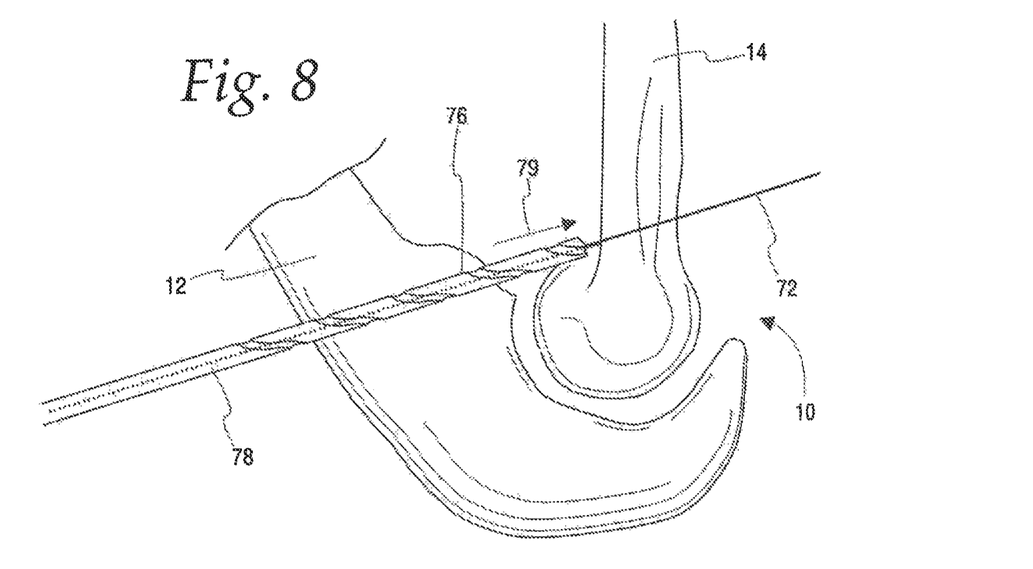

As shown in FIG. 8, a pilot hole is formed through the ulna 20 by directing a cannulated drill bit 78 through the ulna 20 by guiding the drill bit against the guide wire 72 in the direction of the arrow 79. As depicted, the guide wire 72 passes through the drill bit 78 to produce a guided arrangement.

After removing the pilot bit 76, the peg body leading end 62 is advanced through the pilot hole 76 in the direction of the arrow 80. The guide wire 72 slides through the passage 70 as the stabilizing assembly 52 is advanced. The tapered portion 66 facilitates guiding movement of the peg 58 through the ulna 20 as the stabilizing assembly 52 is changed from its starting position, as shown in dotted lines in FIG. 9, into its operative position, as shown in solid lines.

The final movement of the stabilizing assembly 52 into its operative position is achieved by turning the body 60 around its lengthwise axis to cause the threads 68 to engage the ulna 20.

As seen in FIGS. 9 and 10, the humeral head 12 will bear against the tapered portion 66 of the stabilizing assembly 52 with the stabilizing assembly in the operative position. The rounded configuration at the tapered portion 66 avoids hang-up as the humeral head 12 bears thereagainst.

As seen in FIG. 9, the ulna 20 has a length along a first line L1. The length of the implanted body 60 extends along a second line L2 that makes an angle $\alpha$ with the line L1. The angle $\alpha$ is preferably in the range of 35°-65°. In one form, the angle $\alpha$ is on the order of 50°.

As noted above, the stabilizing assembly 52 may be implanted to stabilize the patient's ulnohumeral joint 10 that is deficient as a result of being damaged. The damaged ligaments and muscles may be allowed to heal with the stabilizing assembly 52 implanted, after which the stabilizing assembly can be removed.

Alternatively, the stabilizing assembly 52 may be permanently implanted since it does not interfere with hinging between the humerus 14 and ulna 20.

The foregoing disclosure of specific embodiments is intended to be illustrative of the broad concepts comprehended by the invention.

The invention claimed is:

1. A method of stabilizing a patient's ulnohumeral joint, the method comprising the steps of:
    obtaining a stabilizing assembly having a mounting portion and a buttressing portion; and
    implanting the stabilizing assembly into an operative position wherein the mounting portion of the stabilizing assembly is anchored at a proximal region of the patient's ulna and the buttressing portion is situated to abut a lower head region of the patient's humerus so as to limit subluxation at the ulnohumeral joint while allowing movement between the patient's ulna and humerus at the patient's ulnohumeral joint,
    wherein the step of obtaining a stabilizing assembly comprises obtaining a stabilizing assembly comprising an elongate peg with an elongate body with leading and trailing ends spaced in a lengthwise direction, a trailing end region of the elongate body defining the mounting portion, and a leading end region of the elongate body defining the buttressing portion,
    wherein the step of implanting the stabilizing assembly comprises directing the elongate peg, leading end of the elongate body first, from a starting position externally of the patient's elbow and transversely through the proximal region of the patient's ulna at a region where the patient's coronoid process is located and into the operative position,
    wherein with the elongate peg in the operative position, the leading end region of the elongate body is directly exposed to the lower head region of the patient's humerus and situated so that the lower head region of the patient's humerus is: a) movable relative to the leading end region of the elongate body; and b) directly abuttable to the leading end region of the elongate body to thereby limit subluxation at the patient's ulnohumeral joint.

2. The method of stabilizing a patient's ulnohumeral joint according to claim 1 wherein the elongate peg has mounting threads at the mounting portion and a tapered portion at the leading end region that facilitates guided movement of the elongate peg through the patient's ulna as the elongate body is moved from the starting position into the operative position.

3. The method of stabilizing a patient's ulnohumeral joint according to claim 2 wherein the step of implanting the stabilizing assembly further comprises the step of engaging the mounting threads with the patient's ulna.

4. The method of stabilizing a patient's ulnohumeral joint according to 2 wherein the tapered portion of the stabilizing assembly bears directly against the humerus with the stabilizing assembly in the operative position.

5. The method of stabilizing a patient's ulnohumeral joint according to claim 1 wherein the elongate body has a lengthwise passage extending fully through the elongate body between the leading and trailing ends.

6. The method of stabilizing a patient's ulnohumeral joint according to claim 1 wherein the step of implanting the stabilizing assembly comprises the step of directing a guide wire through the patient's ulna in a predetermined path and into an operative position.

7. The method of stabilizing a patient's ulnohumeral joint according to claim 6 wherein the step of implanting the stabilizing assembly comprises the step of creating a pilot hole through the patient's ulna by directing a cannulated drill through the patient's ulna guidingly against the operatively positioned guide wire.

8. The method of stabilizing a patient's ulnohumeral joint according to claim 7 wherein the step of implanting the stabilizing assembly comprises the step of directing the elongate body leading end first through the pilot hole.

9. The method of stabilizing a patient's ulnohumeral joint according to claim 8 wherein the step of directing the elongate body through the pilot hole comprises the step of using the operatively positioned guide wire to guide the leading end of the elongate body through the pilot hole.

10. The method of stabilizing a patient's ulnohumeral joint according to claim 9 wherein the elongate body has a lengthwise passage extending fully through the elongate body between the leading and trailing ends and the step of using the operatively positioned guide wire to guide the leading end of the elongate body comprises sliding the elongate body along the guide wire with the guide wire extending through the lengthwise passage.

11. The method of stabilizing a patient's ulnohumeral joint according to claim 1 wherein the elongate body has a single piece that defines the mounting and tapered portions.

12. The method of stabilizing a patient's ulnohumeral joint according to claim 1 wherein the stabilizing assembly is implanted to stabilize the patient's ulnohumeral joint that is damaged and destabilized by reason of being damaged and further comprising the step of removing the stabilizing assembly after the stabilizing assembly is implanted for a selected healing period.

13. The method of stabilizing a patient's ulnohumeral joint according to claim 1 wherein the elongate body has a cylindrical cross-sectional configuration.

14. The method of stabilizing a patient's ulnohumeral joint according to claim 1 wherein the patient's ulna has a length along a first line, the length of the elongate body extends along a second line, and the first and second lines make an angle of 35°-65° with respect to each other.

15. The method of stabilizing a patient's ulnohumeral joint according to claim 14 wherein the first and second lines make an angle with each other that icon the order of 50°.

* * * * *